United States Patent [19]

Pitner et al.

[11] Patent Number: 5,302,731
[45] Date of Patent: Apr. 12, 1994

[54] FLUORESCENT PH INDICATORS

[75] Inventors: J. Bruce Pitner, Durham; Randal A. Hoke, Cary, both of N.C.

[73] Assignee: Becton, Dickinson and Company, Franklin Lakes, N.J.

[21] Appl. No.: 912,426

[22] Filed: Jul. 13, 1992

[51] Int. Cl.$^5$ ............................................. C07D 311/90
[52] U.S. Cl. .................................... 549/394; 549/227
[58] Field of Search .............................. 549/227, 394

[56] References Cited

U.S. PATENT DOCUMENTS 4,945,171  7/1990  Haugland ............................ 549/224

OTHER PUBLICATIONS

R. P. Haugland, 1989, "Molecular Probes Handbook," Molecular Probes, Inc., p. 30, Figs. 4,2 and 4.3; supra, pp. 86-88 and 93.
Graber et al., Anal. Biochem., 156, 202-212 (1986).
Kolber et al., J. Immunol. Mtds., 108, 225-264 (1988).

Primary Examiner—Nicky Chan
Attorney, Agent, or Firm—Donna R. Fugit

[57] ABSTRACT

Fluorescent pH indicator compounds which exhibit an increase in fluorescence intensity with decreasing pH. The indicators are derivatives of rhodamine and sulforhodamine type dyes and are particularly useful for measuring pH in acidic environments such as carbon dioxide production by microorganisms and pH of certain acidic intracellular compartments.

2 Claims, 2 Drawing Sheets

FLUORESCENT PH INDICATORS

FIELD OF THE INVENTION

The present invention relates to fluorescent pH indicators and in particular to fluorescent pH indicators which exhibit increasing fluorescence intensity with increasing acidity of the environment being measured.

BACKGROUND OF THE INVENTION

Measurement of pH of solutions, cells and tissues is important in many areas of biological and chemical research and a variety of electrical and spectroscopic techniques have been developed to make such measurements. Measurement of pH by optical indicators, using absorption indicator dyes such as phenolphthalein, has been used routinely in these fields for many years with measurements being made visually or by instrumentation. However, measurement of pH by fluorescence rather than absorbance has the advantage of greater sensitivity, as emitted light is more easily detected than absorbed light. Using fluorescent dyes as pH indicators, it is possible to measure the intracellular pH of single cells by flow cytometry using minimal amounts of the dye.

Many fluorescent dyes useful for measurement of pH are known in the art. The main consideration for a useful fluorescent pH indicator is that the fluorescence intensity of the compound be correlated as reliably as possible with the pH of the medium being measured. An extensive list of readily available fluorescent pH indicators covering the pH range 0 to 14 has been published by G. G. Guilbault in "Practical Fluorescence" (1973).

Many of the fluorescent pH indicators known in the art are phenolic derivatives that undergo absorption shifts to longer wavelength in basic solution, usually with an accompanying increase in fluorescence intensity. Since these rely on deprotonation of a phenol-type functionality to enhance fluorescence intensity, they exhibit a decrease in fluorescence intensity with increasing acidity at longer emission wavelengths. Fluorescein and the umbelliferones are examples of this type of indicator (R. P. Haugland. 1989. "Molecular Probes Handbook" from Molecular Probes, Inc., Eugene, Oreg., pg. 30, FIGS. 4.2 and 4.3). Few fluorescent indicators are known which exhibit increasing fluorescence with increasing acidity, a situation which limits the utility of fluorescent pH indicators in relatively acidic environments such as endosomes and lysosomes.

Seminaphthorhodafluor (SNARF) and seminaphthofluorescein (SNAFL) pH indicators have recently been developed which are useful for measuring pH changes in the range of about 6.3 to 8.6 and are suitable for measurement of intracellular pH. They are benzo[c]xanthene derivatives and are somewhat longer wavelength indicators compared to most other fluorescent pH indicators, making them suitable for use in flow cytometry with excitation by an argon laser at 488 or 514 nm. However, with the exception of SNARF-6 and SNAFL-1, this series of indicators displays the conventional response to pH in which emission intensity decreases with increasing acidity. SNARF-6 and SNAFL-1 exhibit an increase in fluorescence intensity with increasing acidity only at shorter wavelengths, thus limiting detection to more complex and expensive instrumentation. These pH indicators are described in U.S. Pat. No. 4,945,171 and "Molecular Probes Handbook" (R. P. Haugland, 1989, supra, pg. 86-88 and 93; compounds C-1277 and C-1255, respectively). In contrast, the dyes of the present invention exhibit emission spectra in which fluorescence increases with decreasing pH, but this occurs at a longer wavelength emission maximum (i.e., to the right of the isosbestic point). While not wishing to be bound by any particular theory of how the invention operates, Applicants believe the foregoing characteristics suggest that the inventive compounds have a different chemical mechanism for pH dependent fluorescence than SNARF-6 and SNAFL-1.

2',7'-bis-(2-carboxyethyl)-5-(and-6) carboxyfluorescein, (BCECF) is a pH sensitive dye with a side group linked to the fluorescein moiety which consists of two one-carbon spacers attached to carboxylic acids. R. P. Haugland, 1989, supra, pg. 88 and 93, compound B-1151. The side group is similar to that of the present compounds, however, the fluorescein moiety is significantly different structurally from the rhodamine and sulforhodamine moiety of the compounds of the present invention. Further, because BCECF is a derivative of fluorescein, its pH dependent fluorescence intensity is characteristic of fluorescein, i.e., emission intensity decreases with increasing acidity (Graber, et al. 1986. Anal. Biochem. 156, 202–212). BCECF is particularly useful for indicating intracellular pH because it can be synthesized as a BCECF acetoxymethyl ester/monoacetate (BCECF-AM) which is more easily taken up and retained by cells than is BCECF itself (Kolber, et al. 1988. J. Immunol. Mtds. 108, 255-264). Inside the cell BCECF-AM is hydrolyzed by cellular esterases to the acid form which exhibits a pH dependent fluorescence response.

Rhodamine and sulforhodamine type fluorescent dyes are also known in the art and include, for example, rhodamine B, sulforhodamine B, rhodamine 6G, sulforhodamine G, and Texas Red. These dyes are extensively used for fluorescence studies, but they exhibit little, if any, pH dependent fluorescence intensity response. As the inventive compounds are derivatives of rhodamine or sulforhodamine, the pH sensitivity of these compounds was unexpected due to the fact that the parent compounds show pH independent fluorescence. The compounds of the present invention are therefore the first known pH sensitive dyes of the sulforhodamine class. With the possible exception of the SNARF class of dyes, which are hybrids between fluorescein (phenolic) and rhodamine (analine-like) dyes, no rhodamine-based pH sensitive dyes other than those of the present invention are known. In addition, the inventive compounds for the first time provide pH indicators which increase fluorescence intensity with increasing acidity at longer emission wavelengths.

SUMMARY OF THE INVENTION

The inventive fluorescent pH indicators are derivatives of rhodamine or sulforhodamine having the following general structure:

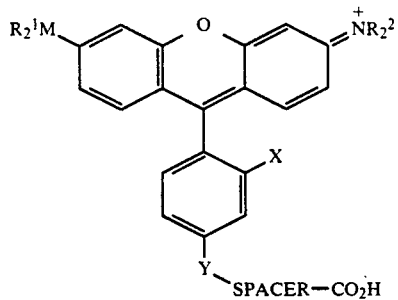

wherein $R^1$ and $R^2$ are hydrogen, alkyl or cycloalkyl; X is $CO_2H$ (or $CO_2^-$) or $SO_3H$ (or $SO_3^-$); Y is —CONH— or —$SO_2$NH—; and SPACER is one or more of —$(CH_2)_n$— wherein n=1-12, cycloalkyl or —CONH—.

Unlike the fluorescent pH indicator dyes of the prior art, these compounds show a fluorescence intensity increase with decreasing pH in the range of pH 7-10 in aqueous solutions at longer wavelength emissions. That is, these compounds have several of the advantages of rhodamine dyes (i.e., high quantum yield, long excitation wavelength and photostability) but unexpectedly also show pH dependent changes in fluorescence intensity which are absent in the prior art rhodamine-type dyes. The longer wavelength characteristics allow the practitioner to use less expensive instrumentation to detect fluorescence and the increased fluorescence response in acidic conditions provides sensitivity in many biological applications where previously known fluorescent pH indicators were unsatisfactory, for example measurement of bacterial $CO_2$ production.

DETAILED DESCRIPTION OF THE INVENTION

Figure 1:
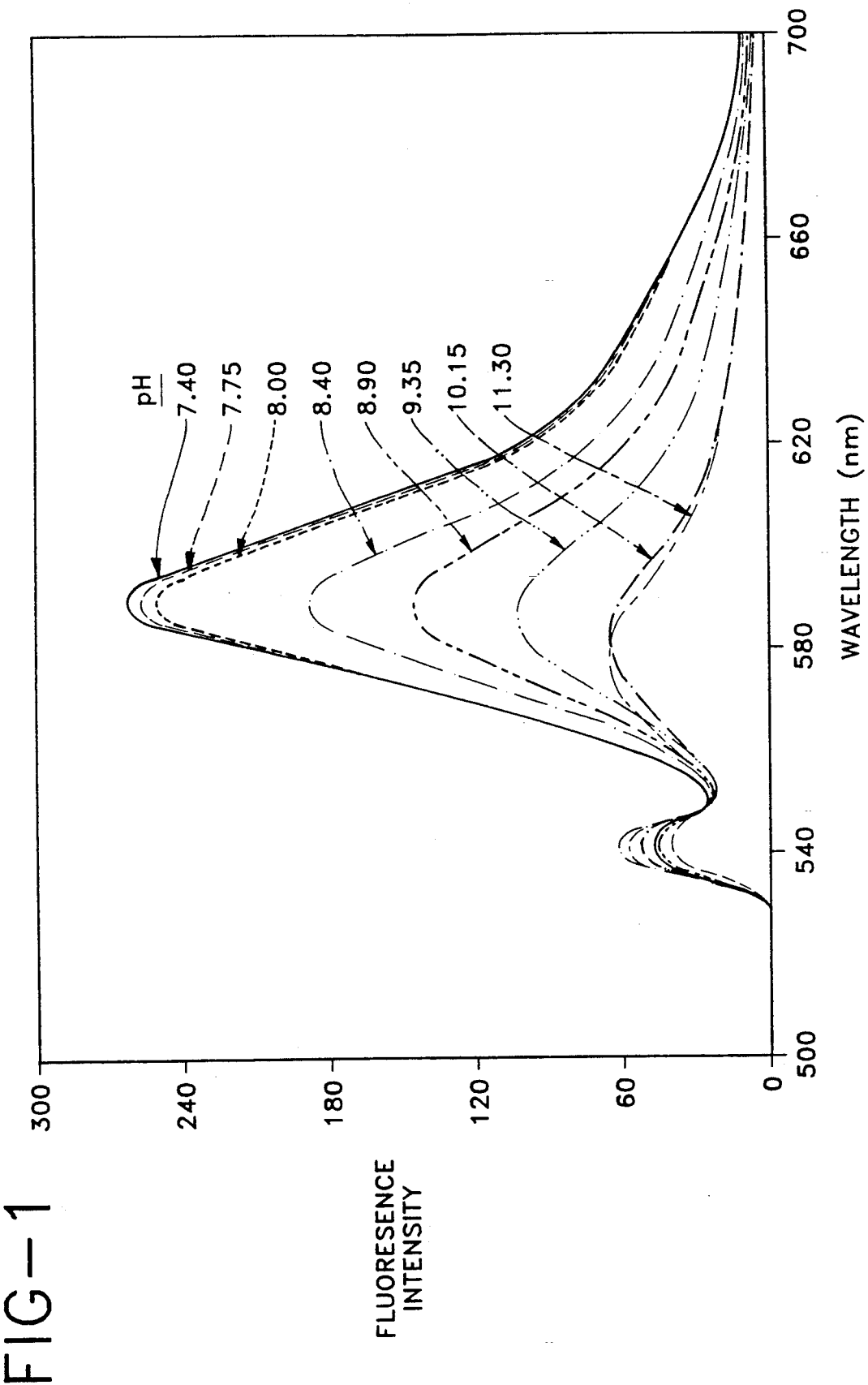
FIG. 1 illustrates the pH dependent fluorescence response of Compound I (SRB-GABA).

The inventive fluorescent pH indicators are derivatives of fluorescent dyes of the rhodamine or sulforhodamine type with a carboxylic acid linked by a "spacer" to the dye. They have the following general structure:

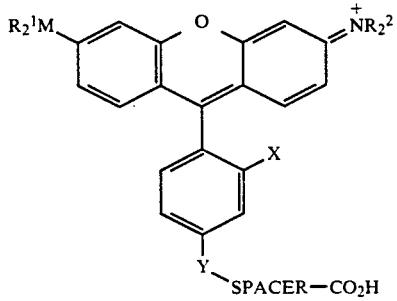

wherein $R^1$ and $R^2$ are hydrogen, alkyl or cycloalkyl; X is $CO_2H$ (or $CO_2^-$) or $SO_3H$ (or $SO_3^-$); Y is —CONH— or —$SO_2$NH—; and SPACER is one or more of —$(CH_2)_n$— wherein n=1-12, cycloalkyl or —CONH—.

The preferred compounds are derivatives of sulforhodamine wherein $R^1$ and $R^2$ are hydrogen, alkyl or cycloalkyl; X is $SO_3H$ (or $SO_3^-$); Y is —$SO_2$NH—; and SPACER is one or more of —$(CH_2)_n$— wherein n=1-12, cycloalkyl or —CONH—.

The most preferred compounds have the structures:

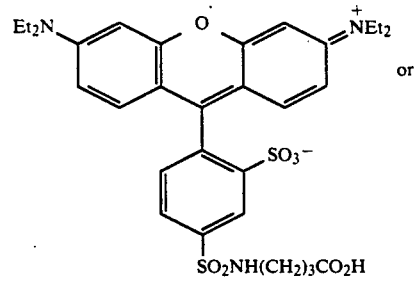

I

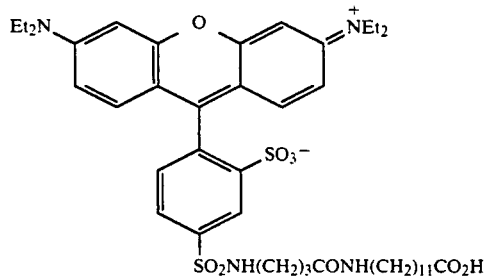

II wherein Et is ethyl. Compounds I and II are derivatives of sulforhodamine B. In Compound I, the Y-spacer-$CO_2H$ moiety is gama amino butyric acid (GABA) linked to the sulfonyl in the para position of sulforhodamine B. In Compound II, the Y-spacer-$CO_2H$ moiety is GABA and 12-amino-dodecanoic acid (ADA) linked to the sulfonyl group.

These pH indicators have a pH detecting range of about pH 7 to about pH 10, Optimally, they may be excited at about 544 nm with emission being measured at about 580-590 nm. This excitation wavelength allows the use of a helium-neon (HeNe) laser for excitation with its accompanying cost advantages and elimination of background due to natural fluorescence. The HeNe laser is also commonly used in immunofluorescence and flow cytometry applications as well as carbon dioxide sensing instruments, making the present pH indicators particularly suited for use in these types of studies.

The compounds of the invention may be synthesized by reacting a rhodamine or sulforhodamine acid chloride with the spacer moiety. In the case of Compound I, sulforhodamine B sulfonyl chloride may be reacted with GABA to form the pH indicator (SRB-GABA). For Compound II, SRB-GABA may be subsequently reacted with N-hydroxysuccinimide (NHS) to form an activated ester which is linked to ADA. It is believed that a pentaglycine derivative may be prepared by reacting SRB-GABA-NHS with pentaglycine in a similar manner.

Certain specific embodiments of the invention are described in the following experimental Examples to illustrate the invention. They are not intended in any way to limit the scope of the invention as defined by the appended claims. Upon study of the specification and the following Examples, modifications and variations of the invention will occur to those skilled in the art without departing from the spirit of the invention and without the exercise of inventive skill. These modifications and variations are also encompassed by the invention.

In the following experimental Examples, analytical TLC was performed on 0.25 mm thick aluminum-backed silica gel plates from EM Science (Cherry Hill, N.J., cat. no. 5534) and 0.2 mm thick Whatman glass backed reverse phase KC-18F plates. Analytical reverse phase HPLC employed a Waters 860 two pump system with photo diode array detection (200–600 nm) and a Brownlee Spheri-5 RP-18 220×4.6 mm column. A linear gradient from 1:1 to 95:5 methanol:water over 30 min was employed for HPLC. Fluorescence spectra were recorded on a Perkin-Elmer LS-5 Fluorometer. NMR spectra were recorded on an IBM/Bruker WP-200SY 200 MHz instrument and chemical shifts are reported relative to tetramethyl silane. Positive ion fast atom bombardment (FAB+) mass spectra were obtained with a VG Trio-2 quadrupole instrument using a glycerol matrix. Sulforhodamine B (SRB) was obtained from Polysciences, Inc. (Warrington, Pa.) and had an HPLC retention time of 2.0 min under the above conditions.

EXAMPLE 1

SYNTHESIS OF SRB-GABA

Sulforhodamine B sulfonyl chloride (0.740 g, 1.28 mmol) and gamma-amino butyric acid (GABA, 1.32 g, 12.8 mmol) were added to a stirred mixture of dimethylaminopyridine (DMAP—Aldrich, 30 mg) and 30% triethylamine (Et3N - Fisher) in water maintained at 0° C. Stirring was continued for 4 h at 0° C., then at room temperature overnight. The solvents were removed by rotary evaporation, resulting in a dark purple/pink residue. A few drops of methanol were added to the residue, followed by 25 mL of $CH_2Cl_2$. The mixture was agitated and the insoluble fraction was separated by vacuum filtration and washed two times with $CH_2Cl_2$. The filtrate was concentrated and chromatographed (flash silica, 1:9:90 to 2:16:80 acetic acid:methanol:$CH_2Cl_2$ gradient). The column fractions were analyzed by TLC (silica, 1:9:90 acetic acid:methanol:$CH_2Cl_2$) and the purest fractions containing the middle eluting pink band were combined. An NMR analysis suggested possible contamination by GABA in some of the fractions so these were refiltered from a suspension in $CH_2Cl_2$, resulting in a total of 89 mg SRB-GABA. The 11% yield is probably due to loss of product in the filtration steps.

Product Analysis

1H NMR (4:1 CDC13-CD3OD) w 1.33 (t,12H), 1.73 (t, 2 H), 2.28 (t, 2 H), 2.93 (t, 2H), 3.62 (q, 8 H), 6.70–7.35 (sulforhodamine H's), 8.29 (d, 1 H), 8.65 (s, 1 H).

13C NMR (4:1 CDC13-CD3OD) w 12.2, 24.7, 30.8, 42.2, 45.8, 95.8, 114.0 ,126.0, 129.6, 130.7, 131.4, 131.9, 140.6, 155.6, 156.0, 157.6.

HPLC retention time 11.4 min.

High resolution FAB+MS [MH+]: $C_{31}H_{38}N_3O_8S_2$. Calculated 644.2100. Found 644.2076.

EXAMPLE 2 pH RESPONSE OF SRB-GABA

The SRB-GABA synthesized in Example 1 was initially expected to be fluorometrically stable to pH due to its derivation from sulforhodamine. However, analysis of the pH vs. UV/visible light spectrum of this compound suggested some pH dependent behavior which was absent in SRB. To determine the pH vs. fluorescence intensity characteristics of the SRB-GABA synthesized in Example 1, the compound was dissolved in 10 mM phosphate buffer, pH 8.0. This was filtered through cotton to reduce scattering and the pH was adjusted with dilute (approximately 0.1 N) sodium hydroxide and hydrochloric acid solutions as required.

A Perkin Elmer LS-5 fluorometer was set as follows:

| Slits: | excitation = 5; emission = 3 |
|---|---|
| Speed: | 120 nm/min. |
| Excitation: | 544 nm |
| Emission: | from 500 to 700 nm |

Surprisingly, the SRB-GABA compound (Compound I) responded to pH changes with changes in fluorescence intensity and showed increasing fluorescence intensity as the pH became more acidic. The results are shown in Table I.

TABLE I

| pH | Fluorescence Intensity |
|---|---|
| 11.30 | 63 |
| 10.15 | 64 |
| 9.35 | 103 |
| 8.90 | 147 |
| 8.40 | 193 |
| 8.00 | 253 |
| 7.75 | 260 |
| 7.40 | 270 |

The above results are depicted graphically in FIG. 1. SRB-GABA exhibits maximal pH vs. fluorescence intensity changes in the pH range of about 8–9.5, and there is approximately a 4-fold change in fluorescence intensity from pH 7.4 to 10.15. The results of this study are depicted graphically in FIG. 1.

EXAMPLE 3

SYNTHESIS OF SRB-GABA-ADA

SRB-GABA NHS ester was prepared essentially as described by Bodansky and Bodansky, "The Practice of Peptide Synthesis," 1984, P. 125. SRB-GABA (140 mg, 0.218 mmol) and N-hydroxy-succinimide (30 mg, 0.26 mmol) were added to a round bottom flask containing 5 mL anhydrous $CH_2Cl_2$. The stirred mixture was cooled in an ice-water bath under argon. Dicyclohexylcarbodiimide (DCC, 54 mg, 0.26 mmol) was added and the mixture was stirred 18 hours at ambient temperature under argon. The resulting mixture was filtered through a coarse glass frit and the solids were rinsed twice with $CH_2Cl_2$. Solvent was removed from the combined filtrate and wash fractions and the residue was chromatographed (flash silica, 1:9 methanol:$CH_2Cl_2$). The desired NHS ester was eluted just ahead of a small amount of unreacted SRB-GABA. Solvent was removed by vacuum to yield 138 mg (85%) of SRB-GABA NHS ester as a pink/purple "glass."

Product Analysis

1H NMR (CDC13/CD3OD) w 1.28 (t, 12H), 1.85 (t, 2H) , 2.63 (t, 2H), 2.71 (br s, 1H), 2.97 (t, 2H), 3.30 (br s, 4H, succinimide—$(CH_2)_2$—), 3.65 (q, 8H), 6.70–7.18

(m, 7H), 8.23-8.55 (m, 2H); FAB+MS: m/z 741 (MH+), 713 (M+—Et), 626 (M+—NHS).

High resolution FAB+MS [MH+]: $C_{35}H_{41}N_4S_2O_{10}$. Calculated 741.2264. Found 741.2260.

The SRB-GABA NHS ester (138 mg, 0.186 mmol) and 12-amino-dodecanoic acid (ADA - Aldrich, 60 mg, 0.28 mmol) were added to a flask containing 5 mL $CH_2Cl_2$ and the mixture was stirred 72 hours under argon at ambient temperature. A TLC analysis (silica, 10% methanol in $CH_2Cl_2$) indicated a new product (Rf=0.28) along with unreacted NHS ester (Rf=0.35). The reaction was not observed to go to completion even with addition of more ADA or DMAP. Solvent evaporation followed by flash chromatography (silica, gradient of 7% to 12% methanol in $CH_2Cl_2$) gave 24 mg of the NHS ester and 64 mg (41%) of fairly pure SRB-GABA-ADA as a pink/purple "glass." This was rechromatographed using the same conditions to obtain pure material for analysis.

Product Analysis

1H NMR (CDC13/CD3OD) w 1.25 (br s, 16H), 1.28 (t, 12H), 1,58 (t, 2H), 1.65 (t, 2H), 2.20 (t, 2H), 2.28 (t, 2H), 2.95 (t, 2H), 3.08 (t, 2H), 3.65 (q, 8H), 6.70-7.18 (m, 7 H), 8.23-8.55 (m, 2H).

HPLC retention time 26.5 min.

High resolution FAB+MS [MH+]: $C_{43}H_{61}N_4S_2O_9$). Calculated 841.3880. Found 841.3869.

EXAMPLE 4 pH RESPONSE OF SRB-GABA-ADA

Figure 2:
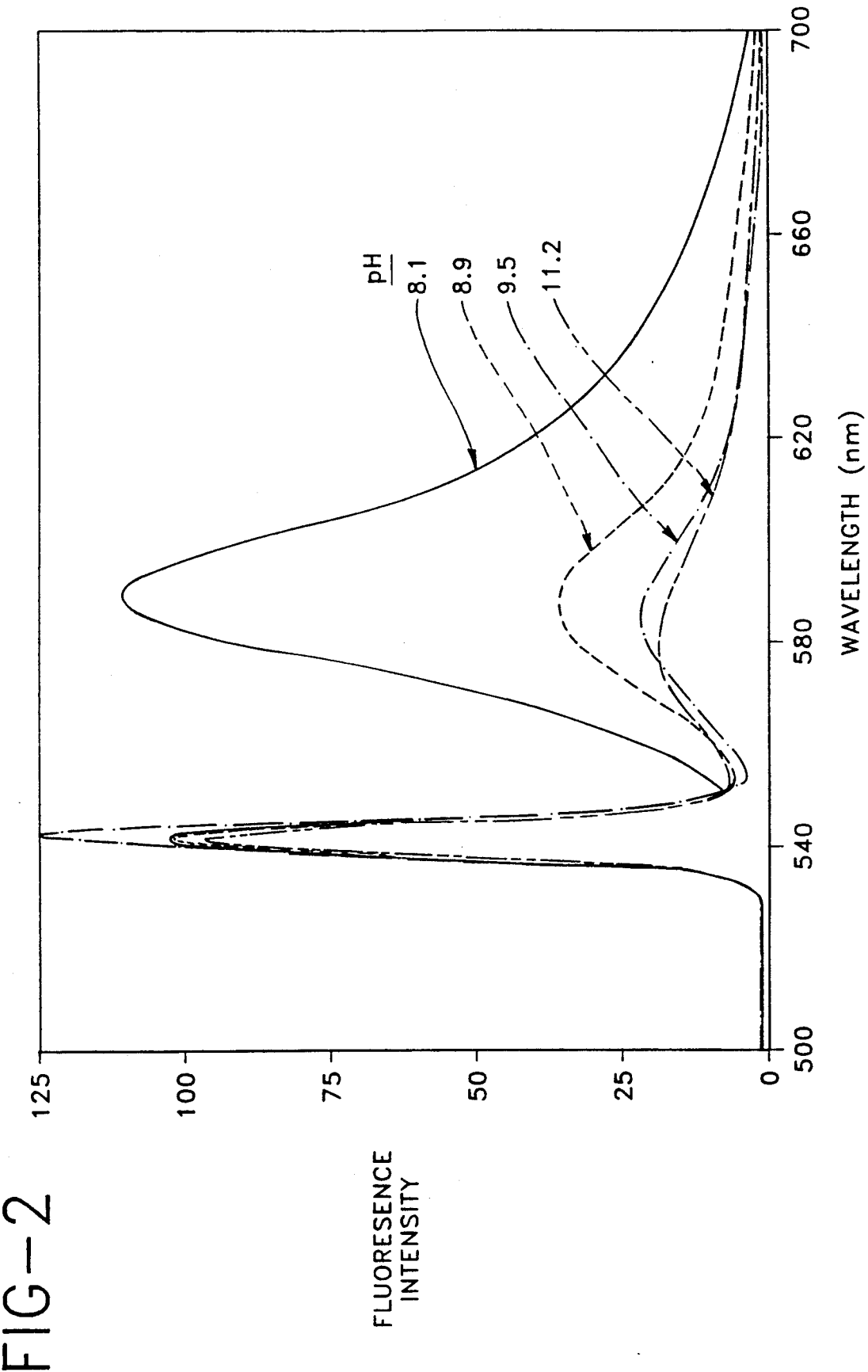
FIG. 2 illustrates the pH dependent fluorescence response of Compound II (SRB-GABA-ADA).

The pH response characteristics of the SRB-GABA-ADA compound synthesized in Example 3 were evaluated essentially as described in Example 2 for SRB-GABA. Fluorescence intensity was measured at pH 11. 2, 9. 5, 8. 9, and 8.1, and the results are depicted graphically in FIG. 2. Again the largest changes in fluorescence intensity were seen between about pH 8 and pH 9.5, with about a 6-fold change in fluorescence intensity from pH 8.1 to 11.2.

What is claimed is:

1. A fluorescent pH indicator compound having the structure:

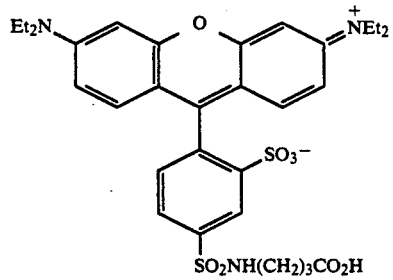

2. A fluorescent pH indicator compound having the structure:

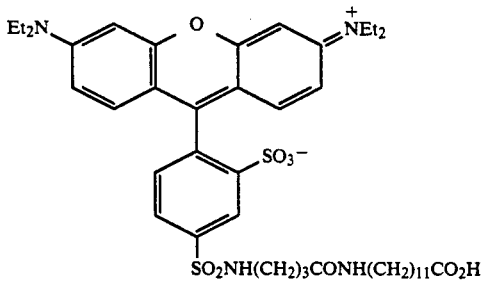

* * * * *